United States Patent
McCauley

(10) Patent No.: US 9,427,383 B2
(45) Date of Patent: Aug. 30, 2016

(54) HYGIENIC BODY WIPE FOR ADULT MALES

(71) Applicant: Yvette Joyce McCauley, Virginia Beach, VA (US)

(72) Inventor: Yvette Joyce McCauley, Virginia Beach, VA (US)

(*) Notice: Subject to any disclaimer, the term of this patent is extended or adjusted under 35 U.S.C. 154(b) by 0 days.

(21) Appl. No.: 14/606,434

(22) Filed: Jan. 27, 2015

(65) Prior Publication Data

US 2015/0216767 A1 Aug. 6, 2015

Related U.S. Application Data

(60) Provisional application No. 61/934,557, filed on Jan. 31, 2014.

(51) Int. Cl.

| | |
|---|---|
| *A61K 8/02* | (2006.01) |
| *A01N 31/04* | (2006.01) |
| *A61K 8/46* | (2006.01) |
| *A61K 8/34* | (2006.01) |
| *A61K 8/97* | (2006.01) |
| *A61Q 19/10* | (2006.01) |
| *A47K 7/03* | (2006.01) |
| *A01N 25/34* | (2006.01) |
| *A01N 37/36* | (2006.01) |
| *A01N 37/40* | (2006.01) |
| *A01N 37/44* | (2006.01) |
| *A61K 8/44* | (2006.01) |

(52) U.S. Cl.
CPC .............. *A61K 8/0208* (2013.01); *A01N 25/34* (2013.01); *A01N 31/04* (2013.01); *A01N 37/40* (2013.01); *A01N 37/44* (2013.01); *A47K 7/03* (2013.01); *A61K 8/345* (2013.01); *A61K 8/44* (2013.01); *A61K 8/463* (2013.01); *A61K 8/97* (2013.01); *A61Q 19/10* (2013.01)

(58) Field of Classification Search
CPC ... A61K 8/0208; A61Q 19/00; Y10T 442/60
See application file for complete search history.

(56) References Cited

U.S. PATENT DOCUMENTS

| | | | |
|---|---|---|---|
| 4,876,035 A | 10/1989 | Breitzke et al. | |
| 6,346,506 B1 | 2/2002 | Julemont | |
| 6,986,897 B1 | 1/2006 | Roberts et al. | |
| 8,499,958 B2 | 8/2013 | Wang | |
| 2002/0176876 A1* | 11/2002 | Harris | A61K 8/03 424/401 |
| 2003/0130636 A1* | 7/2003 | Brock | A61F 13/8405 604/367 |
| 2004/0202635 A1 | 10/2004 | Clausen et al. | |
| 2004/0242097 A1* | 12/2004 | Hasenoehrl | A44B 18/0011 442/59 |
| 2005/0118279 A1* | 6/2005 | Blotsky | A61K 33/00 424/617 |
| 2005/0120497 A1* | 6/2005 | Lynde | A47L 13/20 15/104.94 |
| 2010/0119562 A1* | 5/2010 | Hilliard, Jr. | A61K 8/04 424/401 |
| 2014/0161755 A1 | 6/2014 | Arora et al. | |

OTHER PUBLICATIONS

WebMD, Aloe, (accessed Oct. 22, 2015), pp. 1-3.*
The Personal Formulator, PEG-7 Glyceryl Cocoate, (Feb. 19, 2004), pp. 1-2.*

* cited by examiner

*Primary Examiner* — Brian-Yong Kwon
*Assistant Examiner* — Mark V Stevens
(74) *Attorney, Agent, or Firm* — Winston & Strawn LLP

(57) ABSTRACT

A hygienic body wipe for an adult male. The body wipe comprises a non-woven fabric and a liquid composition that includes a body cleansing agent, a skin conditioning agent, a foaming agent, and water, and a pH of at least about 10.

5 Claims, No Drawings

HYGIENIC BODY WIPE FOR ADULT MALES

The present invention claims the benefit of U.S. Provisional Patent Application No. 61/934,557, filed Jan. 31, 2014. The content of that application is expressly incorporated herein by reference thereto.

BACKGROUND OF THE INVENTION

The present invention relates to a hygienic body wipe that includes a composition specifically formulated for use by adult males.

The patent literature describes numerous fabric wipes that are suitable for both personal hygienic body cleaning and cleaning of hard surfaces. For example, U.S. Pat. No. 6,346,506 teaches an antibacterial non-woven fabric cleaning wipe, and U.S. Pat. No. 6,986,897 teaches an alcohol-free anti-bacterial cleaning wipe.

With respect to body wipes for personal hygienic cleaning, while certain products in the art have been formulated for use with infants and female adults, there is a need for a personal hygienic body wipe with a composition that is specifically formulated to address the physiological requirements and preferences of an adult male. The present invention now satisfies that need.

SUMMARY OF THE INVENTION

The present invention relates to a hygienic body wipe for use by an adult male. The body wipe includes a non-woven fabric and an liquid composition. The liquid composition includes a body cleansing agent that is sodium lauryl sulfate and/or vegetable glycerin. The composition also includes a skin conditioning agent, a foaming agent, and water. The pH of the composition has a pH of at least about 10. In a preferred embodiment, the body cleansing agent is sodium lauryl sulfate. In another preferred embodiment, the body cleansing agent is vegetable glycerin. The composition can also include both sodium lauryl sulfate and vegetable glycerin as body cleansing agents. With respect to the skin conditioning agent, it is preferably selected from fig tree extract, aloe vera leaf extract, sage extract, citrus extract, bamboo extract, resin extract, lavender extract, and sandalwood extract. With respect to the foaming agent, it is preferably TEA-cocoyl glutamate.

In a preferred embodiment, the hygienic body wipe includes a liquid composition with a body cleansing agent in the amount of from about 0.01% to about 30%. If sodium lauryl sulfate is used, it is preferably in an amount from about 1% to about 20%. If vegetable glycerin is used, it is preferably in an amount from about 0.01% to about 5%. The composition also preferably includes from about 50% to about 55% aloe vera extract. The composition also preferably includes water present in an amount of about 8% to about 10%.

The liquid composition of the hygienic body wipe can also include a second skin conditioning agent. In a preferred embodiment, the second skin conditioning agent is Peg 7 glyceril cocoate. The composition can also include other components, such as a preservative, an anti-fungal agent, or anti-bacterial agent. In a preferred embodiment, the preservative is methylparaben. In another preferred embodiment, the preservative is EDTA. In yet another preferred embodiment, the preservative is citric acid or sodium citrate. Other components of the composition can include vitamin E and benzyl alcohol.

The non-woven fabric of the hygienic body wipe includes a liquid-permeable top sheet, a back sheet, and an absorbent core enclosed between the top sheet and back sheet. Preferably, the liquid composition is included in the absorbent core.

In further aspect, the present invention is directed to a process for preparing a hygienic body wipe that can be used by an adult male. The process comprises moisturizing the non-woven fabric with the liquid composition and sealing the body wipe within a package to prevent evaporation of the liquid composition.

DETAIL DESCRIPTION OF THE PREFERRED EMBODIMENTS

The hygienic body wipe of the present invention includes a liquid composition and a non-woven fabric. The body wipe is designed specifically for male adults and for providing clean hygiene by wiping away odor and residues that facilitate growth of bacteria. The liquid composition typically contains water; a body cleansing agent in an amount effective to enhance the cleansing of skin compared to water alone; a skin conditioning agent in an amount effective to ameliorate the skin; and a foaming agent in an amount effective to assist in combining the body cleansing agent and skin conditioning agent in the composition. Thus, the hygienic body wipe provides a dual-action composition for both cleansing the skin and conditioning the skin with moisturizers and deodorants. The hygienic body wipe also includes anti-fungal and anti-bacterial agents to help protect intimate skin areas against common genital irritants, including perspiration, soap, shower gels, and latex prophylactics.

The composition of the hygienic body wipe is a liquid composition. Preferably, the composition is an aqueous formulation, although in other embodiments, suspensions and emulsions can be used. The balance of the composition preferably includes water or purified water. The water is typically present in an amount of about 8% to about 10%, but for some embodiments, the composition can include greater than about 10% water, including from about 10% to about 80% water.

The composition has a pH that is relatively high, and at least higher than any pH that would be suitable for infants or female adults. Preferably, the pH is 10, and in other embodiments, the pH is even greater than 10. The composition is adjusted at this elevated pH using known pH adjusters, including sodium hydroxide, sodium bicarbonate, sodium borate, trisodium phosphate, and the like. The composition can also include an appropriate buffer system to maintain the elevated pH.

The composition also includes at least one body cleansing agent. Preferably, the body cleansing agent is selected from sodium lauryl sulfate and vegetable glycerin. Other body cleansing agents known in the art can also be used, and preferably those that also provide skin moisturizing, softening, and lubricating benefits. Body cleansing agents are present in the composition from about 0.01% to about 30%, preferably from about 0.1% to about 20%, and more preferably from about 1% to about 10%. For example, when sodium lauryl sulfate is selected as the body cleansing agent, it is preferably present in an amount from 1% to about 20%, and more preferably at about 10%. In another example, when vegetable glycerin is selected as the body cleansing agent, it is preferably present in an amount from about 0.01% to 5%, and more preferably at about 0.05%.

The composition also includes at least one skin conditioning agent. Preferably, the skin conditioning agent provides moisturizing, softening, and lubricating benefits to the skin. Preferred skin conditioning agents include natural extracts, for example those of aloe vera leaf, sage, sandalwood, fig tree, citrus, bamboo, resin, lavender, and the like. The skin conditioning agent can also be PEG 7 glyceril cocoate, aloe barbadensis leaf juice, or other similar agent. Skin conditioning agents are present in the composition from about 1% to about 70%, and preferably from about 10% to about 55%. For example, when the skin conditioning agent is aloe vera leaf extract, it is preferably present in an amount from about 40% to about 70%, and more preferably at about 50% to about 55%. In another example, when the skin conditioning agent is sage or sandalwood extract, it is preferably present in an amount from about 1% to about 20%, and more preferably at about 10%. In another example, when the skin conditioning agent is PEG 7 glyceril cocoate, it is preferably present in an amount from about 1% to about 10%, and more preferably at about 1%. In another example, when the skin conditioning agent is aloe barbadensis leaf juice, it is preferably present in an amount from about 1% to about 40%, and more preferably at about 20 to 33%, and most preferably about 28%. This juice is an extract of an aloe plant.

The composition also includes at least one foaming agent. The foaming agent preferably functions as a conditioner for human hair, and/or otherwise functions as a surfactant or has surfactant-like properties. More preferably, the foaming agent is TEA cocoyl glutamate or other similar agent. Preferably, the foaming agent is present in an amount from about 0.01% to about 5%, and more preferably at about 0.08%.

Preservative, anti-fungal, and/or anti-bacterial agents known in the art can also be included in the composition. These include, for example, methylparaben or other similar paraben preservatives, EDTA, citric acid, sodium citrate, and benzyl alcohol. Preferably, these agents are present in an amount from 0.01% to 15%, and more preferably from about 0.1% to about 10%. Other agents that can be included in the composition include vitamin E or other similar topical skin agents, present in an amount from about 1% to about 20% and more preferably at about 10%.

Non-woven fabrics, and the manufacture thereof, for use as a hygienic body wipe are known in the art. The non-woven fabric is preferably layered and textured. For example, the non-woven fabric can include a liquid-permeable top sheet and a back sheet. An absorbent core can be enclosed between the liquid-permeable top sheet and the back sheet, the absorbent core preferably containing the liquid composition. The non-woven fabric is also preferably organic, biodegradable, has low surface tension, and is hypo-allergenic.

After the liquid compositions of the present invention are prepared by simple batch mixing at 25° C. to 30° C., the non-woven fabric is impregnated with the composition by means of a positive impregnation process. The liquid composition is positively fed into the non-woven fabric, for example, through a controlled gear pump and injection bar. Preferably, the liquid composition is fed at a ratio of about 1 to 3 grams of liquid composition to about 1 gram of the non-woven fabric.

The non-woven fabric is preferably made of about 10% to about 90% viscose fibers and about 10% to about 90% polyester fibers. More preferably, the non-woven fabric is made of about 10% to about 95% wood pulp fibers, about 10% to about 40% viscose fibers, and about 10% to about 40% polyester fibers. Even more preferably, the non-woven fabric is made of about 60% to about 95% wood pulp fibers, about 2.5% to about 20% viscose fibers, and about 2.5% to about 20% polyester fibers.

Alternatively, the non-woven fabric can contain about 10% to about 100% rayon. The non-woven fabric may be hydroentangled or air-laided and coated with a binder or extruded and held together with a binder. Such non-woven fabric typically has a basis weight of 90 gsm (gram/square meter) to 10 gsm. Preferably, such non-woven fabric is about 20% to about 100% rayon. Non-woven fabrics that is extruded and held together with a polymer latex binder are particularly preferred. The preferred basis weight for this non-woven fabric is from about 25 gsm to about 40 gsm. The particularly preferred basis weight is about 30 gsm to about 38 gsm. A preferred non-woven fabric is extruded 100% rayon that is held together with a polymer latex binder and has a basis weight of about 30 gsm to about 38 gsm. Suitable latex binders for the non-woven fabric include those polymerized from at least one acrylic monomer, and in particular include those binders comprised of, based upon the total weight of binder, a mixture of from about 70% to about 90% of a first self-crosslinking acrylic emulsion polymer, and preferably such a polymer having a Tg of from about 0° C. to about 10° C. and more preferably about 5° C., and from about 10% to about 30% of a second acrylic emulsion polymer, and preferably such a polymer having a Tg of from about 20° C. to about 40° C., and more preferably about 34° C. In one embodiment, the first self-crosslinking acrylic emulsion polymer is non-ionic, and the second acrylic emulsion polymer is anionic.

The wipes can be packaged by simply being sealed in a pouch made by heat sealing of a plastic material around the moistened wipe. Alternatively, the wipes can be provided in a plastic container either on a single long sheet that is perforated to provide tear off lengths of individual wipes, or even in a plastic container such as that disclosed in U.S. Pat. No. 8,499,958.

EXAMPLES

The following examples illustrate the liquid composition of the hygienic body wipe of the present invention. The exemplified compositions are illustrative only, and do not limit the scope of the invention.

Example 1

Liquid Solution

| | |
|---|---|
| Sodium Lauryl Sulfate | 10% |
| Aloe Barbadensis Leaf Juice | 28% |
| Sage Extract | 10% |
| PEG 7 Glyceril Cocoate | 7% |
| TEA-Cocoyl Glutamate | 5% |
| Methylparaben | 5% |
| Citric Acid | 5% |
| Vitamin E | 10% |
| Benzyl Alcohol | 10% |
| Purified Water | balance (about 10%) |

Adjusted with sodium carbonate to pH 10

Example 2

Liquid Solution

| Vegetable Glycerin | 10% |
|---|---|
| PEG 7 Glyceril Cocoate | 7% |
| Methylparaben | 8% |
| TEA-Cocoyl Glutamate | 5% |
| Citric Acid | 5% |
| *Aloe Vera* Leaf Extract | 55% |
| Purified Water | balance (about 10%) |

Adjusted with sodium carbonate to pH 10

Example 3

Approximately 2 grams of the solutions of Examples 1 and 2 is to be applied to separate woven rayon fiber sheets that were 4" wide and 6" long, and that had a weight of about 36 gsm. The sheets can be packaged in a plastic film, which can be sealed to prevent moisture loss during storage. When it is desired to use such sheets, the package can be opened and the sheets applied to the skin with a wiping motion. The liquid solutions are formulated for male adults and provide clean hygiene by wiping away odor that causes bacteria.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. An adult male hygienic body wipe for an adult male, the body wipe consisting of:
    a non-woven fabric, and
    a liquid composition having a pH of at least about 10 and consisting of:
        water;
        a body cleansing agent of sodium lauryl sulfate in an amount of from about 1% to 10% to enhance the cleansing of skin compared to water alone optionally in combination with vegetable glycerin in an amount from about 0.01% to about 5%;
        a skin conditioning agent of aloe vera extract present in an amount of from about 50% to about 55% and PEG-7 glyceryl cocoate as a further skin conditioning agent in an amount of from about 1% to about 10% to ameliorate the skin; and
        a foaming agent of TEA-cocoyl glutamate in an amount of from about 0.01% to about 5% to assist in combining the body cleansing agent and skin conditioning agent in the composition;
        a pH-adjuster to elevate the pH and/or buffering system to maintain the pH; and
    one or more of a preservative, an anti-fungal agent, anti-bacterial agent, vitamin E or benzyl alcohol.

2. The hygienic body wipe of claim 1, wherein the water is present in an amount of about 8% to about 10%.

3. The hygienic body wipe of claim 1, wherein the preservative is methylparaben, EDTA, citric acid or sodium citrate.

4. The hygienic body wipe of claim 1, wherein the non-woven fabric includes a liquid-permeable top sheet, a back sheet, and an absorbent core enclosed between the top sheet and back sheet; and wherein the liquid composition is included in the absorbent core.

5. A process for preparing a hygienic body wipe product of claim 1 which comprises moisturizing the non-woven fabric with the liquid composition and sealing the moistened body wipe within a package.

* * * * *